(12) United States Patent
Agarwal et al.

(10) Patent No.: US 6,893,453 B2
(45) Date of Patent: May 17, 2005

(54) THERMAL THERAPY PAD WITH VARIABLE HEAT CONTROL

(75) Inventors: Naveen Agarwal, Atlanta, GA (US); Jeffrey Eldon Fish, Dacula, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 118 days.

(21) Appl. No.: 10/322,413

(22) Filed: Dec. 17, 2002

(65) Prior Publication Data

US 2004/0116990 A1 Jun. 17, 2004

(51) Int. Cl.⁷ .................................................. A61F 7/00
(52) U.S. Cl. ...................................... 607/108; 607/114
(58) Field of Search .......................... 607/108–112, 114

(56) References Cited

U.S. PATENT DOCUMENTS

| | | |
|---|---|---|
| 3,802,817 A | 4/1974 | Matsuki et al. |
| 3,849,241 A | 11/1974 | Butin et al. |
| 3,976,049 A | 8/1976 | Yamashita et al. |
| 4,100,324 A | 7/1978 | Anderson et al. |
| 4,106,478 A | 8/1978 | Higashijima |
| 4,186,294 A | 1/1980 | Bender |
| 4,205,685 A | 6/1980 | Yoshida et al. |
| 4,268,272 A | 5/1981 | Taura |

(Continued)

FOREIGN PATENT DOCUMENTS

| | | |
|---|---|---|
| EP | 0370600 A1 | 5/1990 |
| EP | 1121912 A2 | 8/2001 |
| EP | 0835087 B1 | 2/2002 |
| EP | 0889941 B1 | 7/2002 |
| JP | 56-145846 | 11/1981 |
| WO | 98/29079 | 7/1988 |
| WO | 97/49361 | 12/1997 |
| WO | 01/01900 | 1/2001 |
| WO | 01/03625 | 1/2001 |
| WO | 02/56809 | 7/2002 |

OTHER PUBLICATIONS

Patent Abstracts of Japan, Publication No. 04002342A, Jan. 7, 1992.
Patent Abstracts of Japan, Publication No. 05309007A, Nov. 22, 1993.
Patent Abstracts of Japan, Publication No. 63037181A, Feb. 17, 1988.
Patent Abstracts of Japan, Publication No. 07067907A, Mar. 14, 1995.
Patent Abstracts of Japan, Publication No. 07194642A, Aug. 1, 1995.
Patent Abstracts of Japan, Publication No. 08112303A, May 7, 1996.
Patent Abstracts of Japan, Publication No. 10146356A, Jun. 6, 1998.

*Primary Examiner*—Roy D. Gibson
*Assistant Examiner*—Aaron Roane
(74) *Attorney, Agent, or Firm*—James B. Robinson; Nancy M. Klembus

(57) ABSTRACT

There is provided a thermal therapy pad useful in relieving pain and having a plurality of easily removable layers on the side of the pad normally facing the skin. The removal of layers results in increased heat removal or delivery to the skin. The removable layers may be re-attached desirably the user find the pad too hot, or may be moved to the opposite side of the pad, or discarded. The pad may use an iron powder reactive core which reacts exothermically with air to provide heating or water and other reactants that react endothermically. More than one core may be used to further tailor the amount and rapidity of the temperature change.

7 Claims, 4 Drawing Sheets

U.S. PATENT DOCUMENTS

| | | | |
|---|---|---|---|
| 4,282,005 A | 8/1981 | Sato et al. | |
| 4,331,731 A | 5/1982 | Seike et al. | |
| 4,340,563 A | 7/1982 | Appel et al. | |
| 4,366,804 A | 1/1983 | Abe | |
| 4,375,448 A | 3/1983 | Appel et al. | |
| 4,462,224 A | 7/1984 | Dunshee et al. | |
| 4,488,552 A | 12/1984 | McCann et al. | |
| 4,494,278 A | 1/1985 | Kroyer et al. | |
| 4,516,564 A | 5/1985 | Koiso et al. | |
| RE32,026 E | 11/1985 | Yamashita et al. | |
| 4,640,810 A | 2/1987 | Laursen et al. | |
| 4,685,911 A | 8/1987 | Konno et al. | |
| 4,715,918 A | 12/1987 | Lang | |
| 4,741,941 A | 5/1988 | Englebert et al. | |
| 4,747,841 A | 5/1988 | Kuratomi et al. | |
| 4,756,299 A | 7/1988 | Podella | |
| 4,761,324 A | 8/1988 | Rautenberg et al. | |
| 4,818,464 A | 4/1989 | Lau | |
| 4,925,743 A | 5/1990 | Ikeda et al. | |
| 4,963,360 A | 10/1990 | Argaud | |
| 5,030,314 A | 7/1991 | Lang | |
| 5,046,479 A | 9/1991 | Usui | |
| 5,117,809 A | 6/1992 | Scaringe et al. | |
| 5,178,139 A | 1/1993 | Angelillo et al. | |
| 5,277,180 A | 1/1994 | Angelillo et al. | |
| 5,331,688 A | 7/1994 | Kiyohara | |
| 5,342,412 A | 8/1994 | Ueki | |
| 5,366,492 A | 11/1994 | Ueki | |
| 5,382,400 A | 1/1995 | Pike et al. | |
| 5,456,704 A | 10/1995 | Kilcullen | |
| 5,492,754 A | 2/1996 | Chen | |
| 5,527,171 A | 6/1996 | Soerensen | |
| 5,545,197 A | 8/1996 | Bowen | |
| 5,637,165 A | 6/1997 | Chen | |
| 5,658,583 A | 8/1997 | Zhang et al. | |
| 5,674,270 A | 10/1997 | Viltro et al. | |
| 5,702,375 A | 12/1997 | Angelillo et al. | |
| 5,718,955 A | 2/1998 | McGuire et al. | |
| 5,728,057 A | 3/1998 | Ouellette et al. | |
| 5,728,058 A | 3/1998 | Ouellette et al. | |
| 5,728,146 A | 3/1998 | Burkett et al. | |
| 5,730,721 A * | 3/1998 | Hyatt et al. | 604/500 |
| 5,735,889 A | 4/1998 | Burkett et al. | |
| 5,741,318 A | 4/1998 | Ouellette et al. | |
| 5,837,005 A | 11/1998 | Viltro et al. | |
| 5,860,945 A | 1/1999 | Cramer et al. | |
| 5,879,378 A | 3/1999 | Usui | |
| D407,824 S | 4/1999 | Davis et al. | |
| D408,923 S | 4/1999 | Davis et al. | |
| 5,890,486 A | 4/1999 | Mitra et al. | |
| 5,904,710 A | 5/1999 | Davis et al. | |
| 5,906,637 A | 5/1999 | Davis et al. | |
| 5,918,590 A | 7/1999 | Burkett et al. | |
| 5,919,479 A | 7/1999 | Zhang et al. | |
| 5,925,072 A | 7/1999 | Cramer et al. | |
| 5,925,406 A | 7/1999 | McGuire et al. | |
| D412,751 S | 8/1999 | Davis et al. | |
| D417,283 S | 11/1999 | Davis et al. | |
| 5,975,074 A | 11/1999 | Koiso et al. | |
| 5,980,562 A | 11/1999 | Ouellette et al. | |
| 5,984,995 A | 11/1999 | White | |
| D418,606 S | 1/2000 | Davis et al. | |
| 6,019,782 A | 2/2000 | Davis et al. | |
| 6,020,040 A | 2/2000 | Cramer et al. | |
| 6,024,761 A | 2/2000 | Barone et al. | |
| 6,048,326 A | 4/2000 | Davis et al. | |
| 6,074,413 A | 6/2000 | Davis et al. | |
| 6,096,067 A | 8/2000 | Cramer et al. | |
| 6,099,556 A | 8/2000 | Usui | |
| 6,102,937 A | 8/2000 | Cramer et al. | |
| 6,123,717 A | 9/2000 | Davis et al. | |
| D433,145 S | 10/2000 | Davis et al. | |
| 6,127,294 A | 10/2000 | Koiso et al. | |
| 6,146,732 A | 11/2000 | Davis et al. | |
| 6,158,427 A | 12/2000 | McGuire et al. | |
| 6,261,595 B1 | 7/2001 | Stanley et al. | |
| 6,265,631 B1 | 7/2001 | Angelillo et al. | |
| 6,284,266 B1 | 9/2001 | Zhang et al. | |
| 6,303,142 B1 * | 10/2001 | Zhang et al. | 424/449 |
| 6,306,431 B1 | 10/2001 | Zhang et al. | |
| 6,336,935 B1 | 1/2002 | Davis et al. | |
| 6,340,472 B1 | 1/2002 | Zhang et al. | |
| 6,409,746 B1 * | 6/2002 | Igaki et al. | 607/109 |
| 6,465,709 B1 | 10/2002 | Sun et al. | |

* cited by examiner

THERMAL THERAPY PAD WITH VARIABLE HEAT CONTROL

BACKGROUND OF THE INVENTION

The present invention concerns thermal therapy products for warming selected areas of the body to enhance healing or improve comfort.

Thermal therapy products deliver or remove heat for a finite time to a given area once they are activated. Thermal therapy products are used to discourage swelling or to encourage healing after swelling from an injury has receded. They are also used to soothe muscle and joint pain after exercise and for the pain associated with menstruation. These items may also be used to warm a person when chilled and are useful to outdoorsman for outdoor applications.

Previous efforts to deliver thermal therapy have included U.S. Pat. No. 5,658,583 which discloses a drug delivery pad having thermal function with a covering having holes that may be covered and uncovered to control the amount of air reaching the reactive core of the pad. The core reacts with air to produce heat. U.S. Pat. No. 5,919,479 also provides a heated drug delivery pad in which a tape or similar material may be placed on the side of the pad facing the body, and thus reduce the amount of heat reaching the body by increasing the amount of insulation between about the two. U.S. Pat. No. 6,261,595 provides a transdermal drug patch with heating wherein air-permeable and air impermeable layers with holes may be covered to control the temperature. U.S. Pat. No. 4,756,299 provides a heating pad with different sized holes on its opposite sides. The two sides offer the user two different temperatures at which to use the product.

While the above described webs may have performed adequately, they are not as effective or easy to use as may be desired. There remains a need for a thermal therapy product in which the regulation or control of the amount of heat delivery or removal is very simple, easy and effective.

SUMMARY OF THE INVENTION

In response to the discussed difficulties and problems encountered in the prior art, a new thermal therapy pad having removable layers has been developed. The pad has a plurality of layers that may be removed. In a heating pad, this exposes the reactive material in the pad core to more oxygen while simultaneously removing insulation from the pad. In a cooling pad, this removes insulation between the reactive material and the user. The user may thus tailor the rate of heat delivery or removal to his skin to the rate he desires. The layers, once removed, may be reapplied should the user determine the amount of heat being delivered or removed is more than desired. The removed layer may be reapplied on the same side from which it was removed or on the side opposite, or discarded.

DETAILED DESCRIPTION OF THE INVENTION

The present invention is a thermal therapy pad containing a heating or cooling mechanism. The mechanism may be one in which a chemically reactive material reacts exothermically with oxygen. The mechanism may also be one in which reactants react endothermically. The reactants in the case of a heating pad contact one another within the core of the pad and quickly heat the pad to a temperature that is perceived by the user as warm or hot. The pad has an inner side having a plurality of air-permeable layers, the removable layers, that may be sequentially removed from the pad. Upon the removal of each layer, the rate of air reaching the inner portion of the pad increases.

In the case of a heating pad, since reaction with air (oxygen) is the desired method of heating, removing a layer increases the permeability of air to the inner portion of the pad and increases the reaction rate, thus increasing the rate of heat generation. Removal of each layer concomitantly reduces the thickness of the overall layer between the reactive core and the outer surface of the inner side of the pad, thus allowing greater heat flux from the core to the inner side and thereby producing a higher temperature on the inner side. Each removed layer may be reapplied should the user determine that he has removed too many layers and the pad has become too hot for his comfortable use. Each removed layer may also be applied to the away-from-the-body or insulating side of the pad in order to increase the insulation on that side, reducing heat loss and perhaps lengthening the useful life of the pad.

In the case of a cooling pad, removal of each layer does not increase the reactant flow to the core since the reactants are contained within the core and separated by a rupturable membrane. See for example, U.S. Pat. No. 4,462,224 which discloses a pad having two components separated by a seam, which react upon mixing to produce a reduced temperature, and U.S. Pat. No. 5,545,197 which uses two pairs of compartments, each pair having the reactants separated by a rupturable seam. Removal of each layer in this case reduces the amount of insulation between about the core and the user's skin, allowing greater heat flux from the body.

Figure 1A:
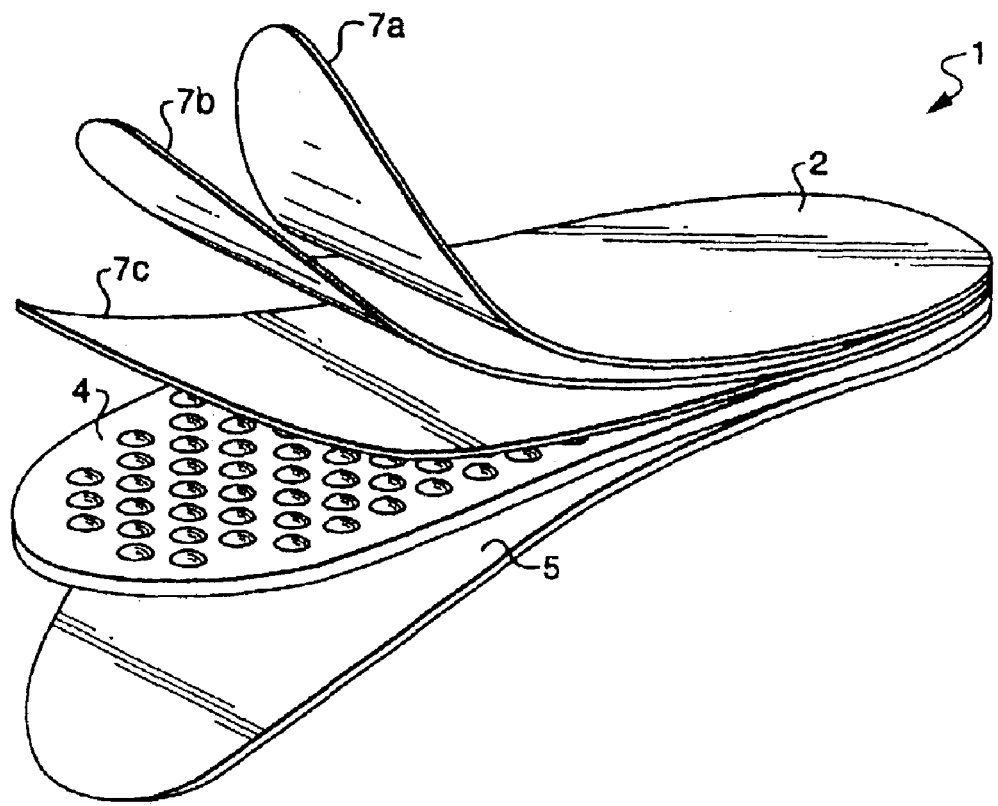
FIG. 1A is a schematic drawing of a thermal therapy pad according to this invention.
Figure 1B:
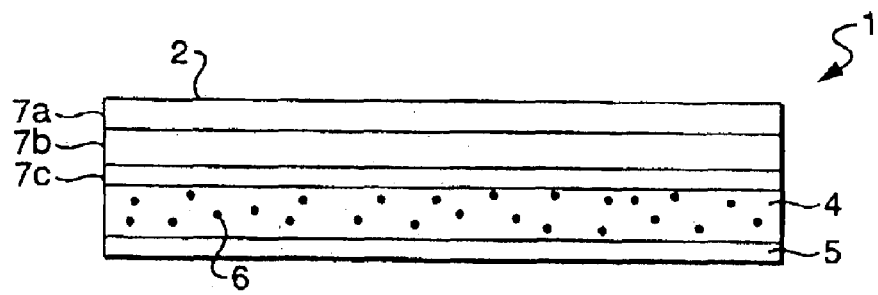
FIG. 1B is a cross-sectional view of a thermal therapy pad according to this invention.

FIG. 1A is a schematic view of a pad of this invention and FIG. 1B is a cross-sectional view of the pad of this invention. The pad 1 has a body-facing or inner side 2 and an away-from-the-body or outer side 3. Located within the pad 1 is the reactive core 4 containing reactive material or mixtures 6. The core 4 has on the outer side 3 an insulating layer 5 to reduce heat flow away from the body. On the inner side 2 the core 4 has a plurality of removable layers 7a, 7b, 7c. The following is a discussion of the reactive core, insulating layer and removable layers.

The Reactive Core:

The reactive core of the pad desirably contains materials that will react endothermically or, alternatively, exothermically on contact with oxygen.

Various exothermically reacting materials are known in the art and include, but are not limited to, iron powders and metal salts of acids. Iron is used desirably in powder form in order to increase the surface area available for reaction. Salts of alkali metals, alkaline earth metals and salts of mineral acids may be successfully used with the iron powder. Examples of suitable metal salts of acids include sodium chloride, potassium chloride, calcium chloride, magnesium chloride, sodium nitrate, potassium nitrate, calcium nitrate, magnesium nitrate, citric and malic acids, and so forth. Useful amounts of reactants in the core are between about 15 and 80 grams, more desirably between about 20 and 60 g, and still more desirably between about 30 and 50 g. The amount of reactant along with the rate of heat generation from the core determines the useful life of the pad and an acceptable pad life is between about 30 and 300 minutes or even longer for use in overnight therapeutic applications. Suitable reactive materials are sold commercially and include, for example, the MYCOAL® Adhesive Patch Iron Powder Pocket containing about 38 grams of reactive material. The MYCOAL® Adhesive Patch Iron Powder Pocket is commercially available from the Grabber Performance Group of Grand Rapids, Mich. It should be noted that the amount of reactant may be increased or decreased depending on the side of the pad desired.

The supply of heat to the skin of a wearer desirably results in increased blood flow and improved circulation in the region of the applied heat, thus increasing healing in the affected area.

The cold pad reactants used desirably include water and a chemical with which water will react endothermically. The endothermically reacting chemical may be any of those known in the art as having a positive enthalpy of solution, including those selected from a group including ammonium nitrate, ammonium bromide, ammonium nitrite, ammonium sulfate, ammonium chloride, ammonium iodide, ammonium sulfamate, sodium nitrate, sodium nitrite, sodium carbonate, sodium bicarbonate, potassium nitrate, potassium nitrite, urea, methylurea, and mixtures of these components.

Figure 2:
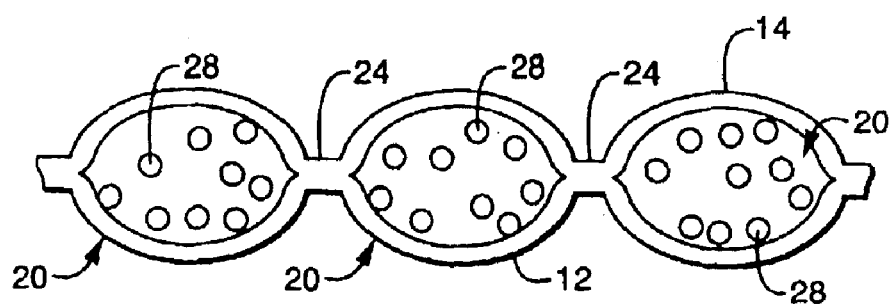
FIG. 2 is a cross-sectional view of a patterned substrate suitable for use in the practice of this invention.

The heating core may be a single pocket of loose reactive material contained within the pad as illustrated by FIG. 1, or may be a plurality of discrete deposits of reactive material distributed in a pattern on a substrate. One example of a suitable patterned substrate may be found in U.S. patent application Ser. No. 10/027,787 as shown in cross section in FIG. 2. FIG. 2 shows two layers 12, 14 fused at spaced apart locations 24. Discrete deposits of reactive material 28 can be contained within the unfused pockets 20. When the reactive material is distributed in this manner, i.e. in discrete pockets, the pad will maintain its integrity and loose particles will not move and shift position as the pad is shipped, stored or used, as may sometimes occur with a large single pocket of reactive material. The pockets may be distributed in various patterns, for example in a square pattern, a hexagon pattern, a diamond pattern and so forth.

The heating core may also be a web containing a relatively uniform distribution of reactive materials within the matrix of the web. This embodiment may be made according to various processes such as, for example, spunbond, meltblown, coform or airlaid processes.

As noted above, the core for cooling applications has a rupturable membrane separating water and the other reactant. The rupturable membrane is broken when cooling is desired.

The coform process is one in which at least one meltblown diehead is arranged near a chute through which the reactive materials are added to the web while it is forming. Other materials such as pulp and natural or synthetic polymer fibers may also be added to the web. Exemplary coform processes are described in U.S. Pat. Nos. 4,818,464, 4,100, 324 and U.S. Pat. No. 4,741,941.

The airlaid process involves the production of a nonwoven web in which various materials are suspended in an air stream and deposited onto a forming wire. These materials can include the reactive materials discussed above as well as pulp and natural and synthetic polymer fibers. Examples of airlaid processes include but are not limited to those described in U.S. Pat. Nos. 4,640,810, 4,494,278, 5,527,171 and 4,375,448.

The Insulating Layer:

The insulating layer may be made from any material having a relatively low heat flux, i.e., desirably a heat flux below that of the inner removable layers. The insulation layer is desirably between about 2 and 10 mm thick, or more desirably between about 2 and 7 mm thick and most desirably about 4 mm thick. The basis weight of this layer is desirably between about 30 and 800 grams per square meter (gsm), more desirably between about 150 and 600 gsm and most desirably between about 300 and 500 gsm.

Suitable materials for the insulating layer include foams, knitted fabrics, woven fabrics and nonwoven fabrics such as coform webs, spunbond and meltblown fiber webs, bonded carded webs, airlaid webs and combinations and laminates of such materials. The making of various examples materials is discussed in more detail below.

The production of foams, for example, is described in U.S. Pat. No. 4,761,324. Commercial examples of suitable foams include, but are not limited to those produced by the General Foam Corporation of Paramus, N.J. Such foams are polyurethane foams under the trade designation "4000 Series". Foams that are closed-cell are desired over those that are open-celled since closed-cell foams are relatively less permeable to air flow.

Meltblown fibers for web-making are formed by extruding a molten thermoplastic material through a plurality of fine, desirably circular, die capillaries as molten threads or filaments into a high velocity gas (e.g. air) stream which attenuates the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849, 241 to Butin. Suitable meltblown fiber webs are made from various olefins and olefin co-polymers like polyethylene, polypropylene, polybutylene etc. Meltbown fibers may also be made from elastic polymers.

A suitable coform web may be made from meltblown fibers with pulp as discussed above. Coform materials for the production of the insulating layer may have from 20 to 80 weight percent meltblown fiber, with the balance pulp. The weight ratio of the meltblown and pulp may thus be between about 20/80 and 80/20. More desirably a ratio of between about a 30/70 and 70/30 may be used, or still more desirably a ratio of between about 40/60 and 60/40 may be used. A suitable airlaid web made by the methods discussed above may be made using the same materials and in the same proportions as the coform web.

Suitable spunbond fiber webs may be made, like meltblown webs, from polyolefins like polypropylene, polybutylene and so forth. Spunbond fibers are small diameter fibers which are formed by extruding a molten thermoplastic material as filaments from a plurality of fine, desirably circular, capillaries of a spinnerette with the diameter of the extruded filaments then being rapidly reduced as by, for example, eductive drawing or other well known spunbonding mechanisms. The production of spunbonded nonwoven webs is illustrated in patents such as, for example, in U.S. Pat. No. 5,382,400 to Pike et al., U.S. Pat. No. 4,340,563 to Appel et al., U.S. Pat. No. 3,802,817 to Matsuki.

Bonded carded webs are made from staple fibers which are sent through a combing or carding unit, which breaks apart and aligns the staple fibers in the machine direction to form a desirably machine direction-oriented fibrous nonwoven web.

Once a web is formed, it is desirably bonded to provide structural integrity by one or more of several methods, such as powder bonding and pattern bonding. Powder bonding involves the distribution through the web of an adhesive which is then activated, desirably by heating the web and adhesive with hot air. Pattern bonding is a process in which heated calender rolls or ultrasonic bonding equipment are used to bond the fibers together. Pattern bonding is performed desirably in a localized bond pattern, though the web can be bonded across its entire surface, if so desired. Other bonding processes include through-air bonding, stitch bonding and microwave bonding.

The Removable Layers:

The removable layers may be made by the same processes as used to make the insulating layer, though the removable layers are desirably thinner and lighter weight than the insulating layer since there is a plurality of them. The removable layers may additionally be an air-permeable film such as a film filled with, for example, calcium carbonate, clays, silica, alumina, barium sulfate, sodium carbonate, talc, magnesium sulfate, titanium dioxide, zeolites, aluminum sulfate, diatomaceous earth, magnesium sulfate, magnesium carbonate, barium carbonate, kaolin and so forth. Such filled films are generally referred to as microporous films.

The removable layers may themselves each be laminates; combining two or more single layers such as film layers, spunbond layers, meltblown layers, coform or airlaid layers and bonded carded web layers, into one removable layer. The removable layers of a pad need not be identical, as varied types of removable layers may afford the user even greater flexibility in temperature control.

The removable layers are desirably between about 0.01 and 5 mm thick, more desirably between about 0.02 and 1 mm thick. The pad of this invention desirably has between about 2 and 8 removable layers, more desirably between about 2 and 5 removable layers, placed one atop the other on the reactive core on the side opposite that of the insulating layer.

It is important that the removable layers in the heating pad be permeable to air so that the reactive material in the core will be able to exothermically react, but not so permeable that the removal of a layer will have no effect on the rate of reaction. Each removable layer, therefore, is desirably less permeable to air than is the outer layer of the reactive core.

Figure 3:
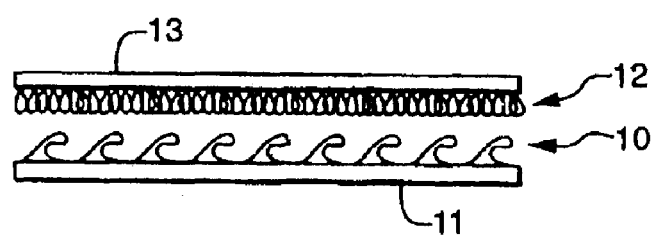
FIG. 3 is a drawing of a typical hook and loop fastener, showing partial engagement of the hooks and loops that are attached to substrates.

Each removable layer may be detachably/removably attached to the layer adjacent to it by the use, for example, of hook and loop type fasteners like those sold under the trade name VELCRO, available from Velcro USA, of Manchester, N.H. A typical hook and loop fastener arrangement is shown in FIG. 3. As shown in FIG. 3, hooks 10 are formed on or permanently attached to a first substrate 11. Loops 12 are formed on or permanently attached to a second substrate 13. When the two substrates 11, 13 are brought together in an orientation where the hooks 10 can contact the loops 12, the hooks 10 and loops 12 become engaged with one another, thus holding the substrates 11, 13 together. The hooks 10 and loops 12 may be disengaged through the use of sufficient peeling force. The peeling force or "peel strength" of a fastener is the amount of tensile force needed to pull the two substrates apart and is discussed below. The peel strength of hook and loop fasteners suitable for use in the practice of this invention is between about 2 and 100 grams, more desirably between about 5 and 50 g and most desirably between about 5 and 25 g.

The removable layers may alternatively be attached with a pressure sensitive adhesive. Exemplary adhesives are commercially available under the SCOTCH brand by 3M Corporation as adhesive transfer tape, item numbers 924, 926, 969 and 928. The peel strength values for adhesive attachment is often below that of hook and loop type fasteners though are sufficiently high so as to maintain two substrates together under normal use conditions.

Any other method of releasably attaching the layers is suitable provided it allows a user to remove each layer individually without damaging the pad or the layer.

Values for peel strength are obtained using a specified width of fabric, clamp jaw width and a constant rate of extension. The test uses two clamps, each having two jaws with each jaw having a facing in contact with the sample, to hold the material in the same plane, desirably vertically, separated by 5.1 cm (2 inches) to start. The sample size is 10.2 cm (4 inches) wide by as much length as necessary to delaminate enough sample length. The jaw facing size is 2.5 cm (1 inch) high by at least 4 inches wide, and the constant rate of extension is 300 mm/min. The sample is delaminated by hand a sufficient amount to allow it to be clamped into position and the clamps then move apart at the specified rate of extension to pull the laminate apart. The sample specimen is pulled apart at 180° of separation between about the two layers and the peel strength reported as an average of peak load in grams. Measurement of the force is begun when 16 mm of the laminate has been pulled apart and continues until a total of 170 mm has been delaminated. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or the Thwing-Albert Model INTELLECT II available from the Thwing-Albert Instrument Co., 10960 Dutton Rd., Phila., Pa. 19154, may be used for this test. Results are reported as an average of three specimens and may be performed with the specimen in the cross direction (CD) or the machine direction (MD).

One example of a removable layer is laminate having a spunbond web layer, a meltblown web layer, a second spunbond layer and a second meltblown layer made according to the multiple processes discussed above, and ultrasonically bonded together. The basis weight of each spunbond layer may be about 15 gsm and of each meltblown layer about 34 gsm and all layers may be made from polypropylene. The removable layers may be about 13 cm by 10 cm and may be adhesively bonded to each other and to the core around the periphery of each removable layer with, for example, SCOTCH brand adhesive transfer tape, item number 924. The insulation layer may be identical to the removable layers, i.e., four layers of a four layer laminate, of the same size and basis weight as the removable layers, for a total basis weight of about 393 gsm.

Figure 6:
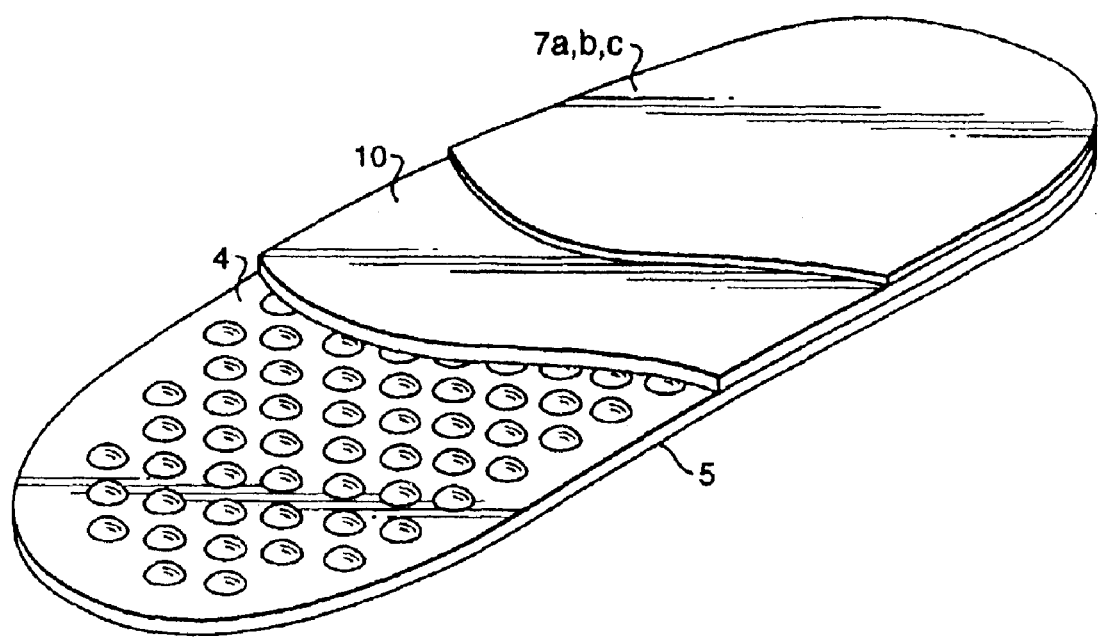
FIG. 6 is schematic drawing of an alternative embodiment in which the heating pad has a second, rapid-heating reactive core adjacent to the first reactive core.
Figure 7:
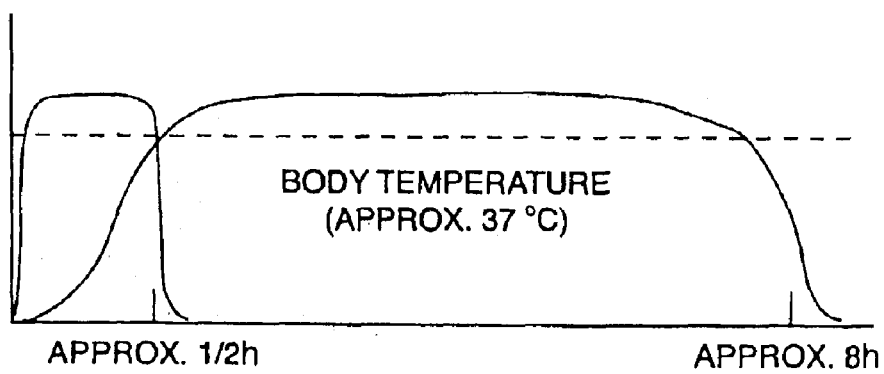
FIG. 7 is a graph of the temperatures projected for the alternative embodiment of FIG. 6 indicating the rapid heating of the second core and gradual heating of the first reactive core.

The thermal therapy pad of this invention may, as an alternative heating embodiment, have a second reactive core positioned over the first reactive core. This second reactive core may be placed on the inner side. This embodiment is illustrated in FIG. 6. The second reactive core 10 may be made from a different composition than that of the first reactive core 4 so that it heats more rapidly than the first core 4. This rapid heating can provide quick delivery of treatment for pain while the slower, but longer lasting, first core reaches the proper temperature. Rapid heating for a short time period may be attained by careful selection of reactant particle size, oxygen availability and reactant mixture composition. FIG. 7 shows a graphical representation of the temperature profile of such an alternative embodiment with temperature on the Y-axis and time on the X-axis. As can be seen from FIG. 7, it's believed that the second reactive core, the temperature of which is represented by the first peak on the graph, will rapidly reach its peak temperature, while the first core will slowly reach its peak temperature some time after the second core peaks. In this manner the alternate embodiment can provide both rapid relief and long term soothing heat for damaged or strained muscles and joints.

Testing and Results:

A heating pad was made using as the reactive core a MYCOAL® Adhesive Patch Iron Powder Pocket with about 38 grams of reactive material and dimensions of 13 cm by 9.5 cm. There were three removable layers and each was a layer taken from another MYCOAL® Adhesive Patch. In the test below, the test surface was a polyethylene sheet on top of a typical ceramic lab bench.

Figure 4:
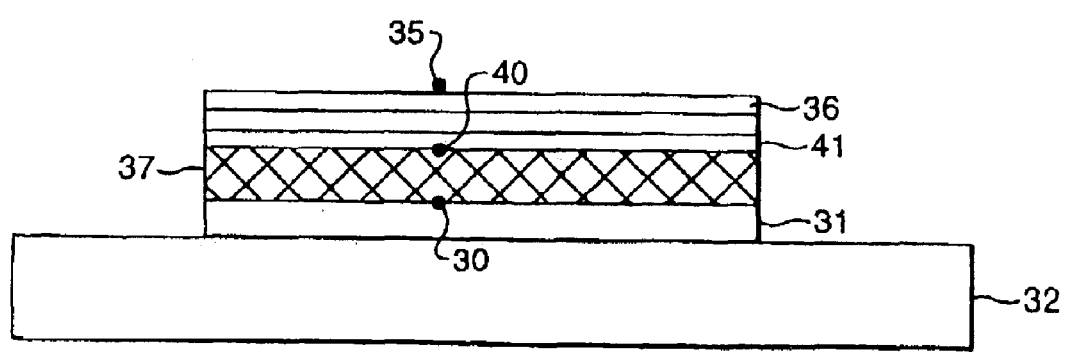
FIG. 4 is a cross-sectional representation of a test configuration for the pad of the invention.

The test arrangement is illustrated in FIG. 4. In FIG. 4, there is a first thermocouple 30 between about the insulating layer 31 and the test surface 32 upon which the insulation layer 31 rested. A second thermocouple 35 was placed on the outside of the farthest removable layer 36 from the reactive core 37. The farthest removable layer 36 would be the outer surface on the inner side (the side towards the wearer) of a pad in actual use. A third thermocouple 40 was placed between the reactive core 37 and the closest removable layer 41.

Figure 5:
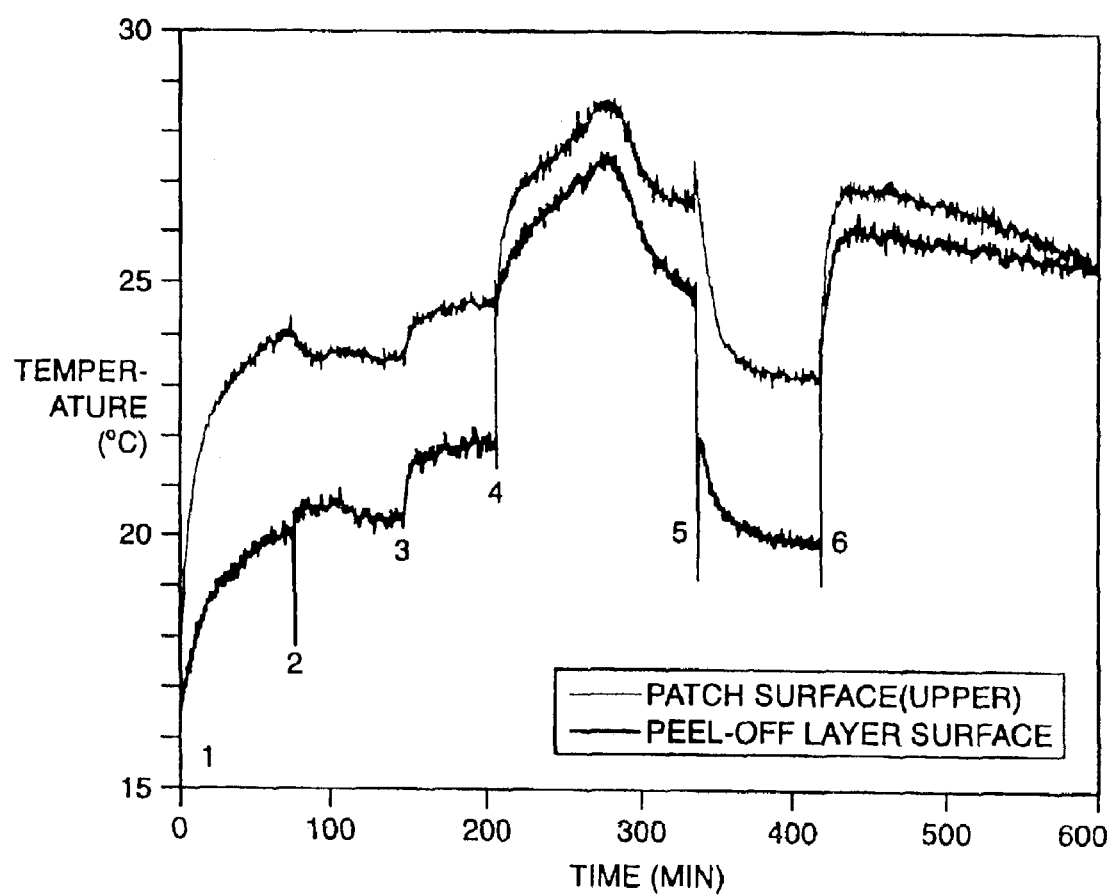
FIG. 5 is graph of the temperatures recorded during a test of a heating pad, showing the change in inner side surface temperature of the pad as each removable layer is removed.

In this test, the temperatures were allowed to stabilize after the reactive core was exposed to air. FIG. 5 shows in graphical form the temperatures recorded by the thermocouples in the testing described above as well as noting what occurred at each point in the test. After the temperatures had stabilized, one of the removable layers was removed and the temperatures allowed to stabilize, at point 2 in FIG. 5. This procedure was repeated a two more times and noted as 3 and 4 in FIG. 5. The three removable layers were then placed back in their original positions on the pad and the temperatures allowed to stabilize, at point 5 in FIG. 5. Lastly, all three removable layers were again removed and the temperatures allowed to stabilize at point 6 in FIG. 5.

In FIG. 5, the second thermocouple 35 temperature is denoted by line number 2 and the third thermocouple 40 temperature by line number 3. The x-axis indicates time in minutes and the y-axis indicates temperature in degrees Celsius. As can be seen by the graph in FIG. 5, each time a removable layer was removed, the temperature of the inner side increased. When all three layers were reapplied the surface temperature dropped significantly and when they were all removed the temperature increased significantly.

As can be seen from the results, the pad of the invention has a change in temperature on the outer surface on the inner side (the side towards the wearer) of between about 0.5 and 50° C. as each layer is removed. This temperature change is desirably between 0.5 and 3° C. upon the removal of each layer. This allows a great deal of flexibility and control, i.e. "tunability" of the temperature by the wearer of the inventive pad. It should also be noted that this feature is useful because the pad may be used under various ambient conditions. These conditions may change the user's perception of heat and cold, or the amount of heat perceived to be needed to be supplied or removed. A small increase in skin temperature, for example, may be perceived to be sufficient if the ambient temperature is very low.

As will be appreciated by those skilled in the art, changes and variations to the invention are considered to be within the ability of those skilled in the art. Examples of such changes are contained in the patents identified above, each of which is incorporated herein by reference in its entirety to the extent it is consistent with this specification. Such changes and variations are intended by the inventors to be within the scope of the invention.

What is claimed is:

1. A thermal therapy pad comprising a first reactive core which undergoes a reaction, an insulating layer attached to a first side of said reactive core, and a plurality of adhesively, detachably attached removable layers attached to a second side of said reactive core, wherein said removable layers each comprise a layer selected from the group consisting of spunbond webs, meltblown webs, coform webs, airlaid webs, bonded carded webs, filled films and combinations and laminates thereof.

2. The pad of claim 1 wherein said removable layers each comprise a laminate of spunbond webs and meltblown webs.

3. A thermal therapy pad comprising a first reactive core having between about 20 and 60 grams of a mixture of iron powder and an alkali metal salt, which undergoes an exothermic reaction upon exposure to air, an insulating layer having a basis weight between about 300 and 500 gsm, attached to a first side of said reactive core, and between about 2 and 5 detachably attached removable layers attached to a second side of said reactive core, wherein each of said removable layers comprises a four layer laminate of a first spunbond web, a first meltblown web, a second spunbond web and a second meltblown web.

4. The pad of claim 3 wherein said removable layers are detachably attached with a pressure sensitive adhesive.

5. The pad of claim 4 wherein said detachably attached removable layers may be attached to said insulating layer after detachment from said second side of said reactive core.

6. The pad of claim 5 wherein said insulating layer is made by a process selected from the group consisting of airlaying, coforming, bonded carded web and nonwoven processes.

7. A thermal therapy pad comprising a first reactive core having between about 30 and 50 grams of a mixture of iron powder and an alkali metal salt, which undergoes an exothermic reaction upon exposure to air, a closed-cell foam insulating layer having a basis weight between about 300 and 500 gsm, attached to a first side of said reactive core, and between about 2 and 5 detachably attached removable layers attached to a second side of said reactive core, wherein each of said removable layers has a thickness between about 0.25 and 2 mm, is attached with a pressure sensitive adhesive, and comprises a three layer, ultrasonically bonded laminate of a spunbond web, a meltblown web and a filled film.

* * * * *